United States Patent
Mennen (10) Patent No.: US 6,852,886 B2
(45) Date of Patent: Feb. 8, 2005

(54) PROCESS FOR THE PREPARATION OF UREA

(75) Inventor: Johannes Henricus Mennen, Meijel (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/474,734

(22) PCT Filed: Apr. 24, 2002

(86) PCT No.: PCT/NL02/00263

§ 371 (c)(1),
(2), (4) Date: Oct. 14, 2003

(87) PCT Pub. No.: WO02/090323

PCT Pub. Date: Nov. 14, 2002

(65) Prior Publication Data

US 2004/0116743 A1 Jun. 17, 2004

(30) Foreign Application Priority Data

May 3, 2001 (NL) .............................. 1017990

(51) Int. Cl.⁷ ............................................ C07C 273/04
(52) U.S. Cl. ............................ 564/67; 564/70; 564/71; 564/72; 422/187; 422/188; 422/198; 422/200

(58) Field of Search ............................. 564/67, 70, 71, 564/72; 422/187, 188, 198, 200

(56) References Cited

U.S. PATENT DOCUMENTS 6,118,023 A * 9/2000 Jonckers et al. .............. 564/70

FOREIGN PATENT DOCUMENTS

NL  8 900 152  8/1990

* cited by examiner

*Primary Examiner*—Peter G O'Sullivan
(74) *Attorney, Agent, or Firm*—Mayer, Brown, Rowe & Maw LLP (57) ABSTRACT

Process for the preparation of urea from ammonia and carbon dioxide in which a urea synthesis solution containing urea, ammonium carbamate and unconverted ammonia is formed in a synthesis zone, a part of the urea synthesis solution being transferred from the synthesis zone to a medium-pressure treatment zone operating at a pressure of 1–4 MPa, and a gas stream from the medium-pressure treatment zone being absorbed into the low-pressure ammonium carbamate solution from the urea recovery section.

10 Claims, 4 Drawing Sheets

PROCESS FOR THE PREPARATION OF UREA

CROSS REFERENCE TO RELATED APPLICATION

This application is the National Phase of International Application PCT/NL02/00263 filed Apr. 24, 2002 which designated the U.S., and that International Application was published under PCT Article 21(2) in English.

The invention relates to a process for the preparation of urea from ammonia and carbon dioxide.

Urea can be prepared by introducing excess ammonia together with carbon dioxide into a synthesis zone at a high pressure (for example 12–40 MPa) and elevated temperature (for example 160–250° C.), which first results in the formation of ammonium carbamate according to the reaction:

$$2NH_3+CO_2 \rightarrow H_2N-CO-ONH_4$$

Dehydration of the ammonium carbamate formed then results in the formation of urea according to the equilibrium reaction:

$$H_2N-CO-ONH_4 \leftrightharpoons H_2N-CO-NH_2+H_2O$$

The theoretical maximum conversion of ammonia and carbon dioxide into urea is determined by the thermodynamic position of the equilibrium and depends on, for example, the $NH_3/CO_2$ ratio (N/C ratio), the $H_2O/CO_2$ ratio and the temperature. From the above reaction equations it can be deduced that the use of an excess of water in the synthesis zone has a negative effect on the theoretical maximum conversion.

Upon the conversion of ammonia and carbon dioxide into urea in the synthesis zone a urea synthesis solution is obtained as reaction product containing substantially urea, water, ammonium carbamate and unconverted ammonia.

Besides a urea synthesis solution, in the synthesis zone also a gas mixture may be formed of unconverted ammonia and carbon dioxide together with inert gases, the so-called synthesis gas. The inert gases present in the synthesis gas usually originate from the air supplied to the equipment to improve its corrosion resistance. Ammonia and carbon dioxide are removed from the synthesis gas in a scrubber zone before the synthesis gas is vented to the atmosphere. This ammonia and carbon dioxide are preferably returned to the synthesis zone.

The synthesis zone may consist of separate zones for the formation of ammonium carbamate and urea. These zones may, however, also be combined in one apparatus. The synthesis may be carried out in one or two reactors. When use is made of two reactors, the first reactor may for example be operated using almost fresh raw materials and the second one using raw materials entirely or partly obtained elsewhere in the process that are recycled to the synthesis zone.

The conversion of ammonium carbamate into urea and water in the synthesis zone can be effected by ensuring a sufficiently long residence time for the reaction mixture in this zone. The residence time will generally be longer than 10 minutes, preferably longer than 20 minutes. The residence time will generally be shorter than 3 hours, preferably shorter than 1 hour.

Urea production facilities are designed for a certain capacity. As a rule it is only to a limited extent possible to increase the capacity of an existing urea production facility by increasing the amounts of starting materials and increasing the throughput of process streams. If it is desired to increase the capacity of a facility by increasing the throughput of the process streams, then it should be ensured that good efficiencies are achieved with the increased process streams in the various process steps. This holds in particular for the process steps that are carried out in the high-pressure section of the urea production facility.

The high-pressure section of a urea production facility operating according to the so-called stripping process substantially consists of a synthesis zone in which the urea synthesis solution is prepared, a stripping zone in which the urea synthesis solution is stripped in countercurrent with one of the raw materials and/or heat, a condensation zone in which the gases released in the stripping zone are condensed and a scrubber zone in which ammonia and carbon dioxide are removed from the synthesis gas.

Bottlenecks in this high-pressure section may in particular be the stripping treatment of the urea synthesis solution in the stripping zone and the condensation in the condensation zone of the gases obtained in the stripping operation. The reason for this is that, if the liquid load of the stripping zone is raised too much, the stripping effect is largely lost due to, among other things, flooding. Flooding means that the liquid film inside the tubes in the stripper is decomposed and part of the liquid is entrained by the exiting gas stream. This strongly reduces the stripping efficiency. The increase in the amounts of starting materials has little effect on the capacity of the synthesis zone. The shorter residence time resulting from the higher throughput does have as a consequence that the ammonium carbamate content of the urea synthesis solution increases somewhat, so that more steam is needed in the stripping zone for decomposition of the ammonium carbamate. It is, therefore, the stripping zone that is the limiting factor rather than the synthesis zone.

It should remain possible, also at the increased gas mixture feed, for the heat released upon condensation in the condensation zone of the gas mixture obtained in the stripping operation to be converted into steam suitable for use elsewhere in the urea process using the existing heat-exchanging area. It is found, however, that an increased feed of gas to be condensed results in a too low steam pressure, as a consequence of which this steam can no longer be used elsewhere in the urea process.

Said bottlenecks are largely responsible for the fact that it is only to a limited extent possible to expand the capacity of an existing facility without modification or replacement of expensive high-pressure equipment. These bottlenecks are encountered in particular when use is made of so-called combination reactors for the preparation of urea. Combination reactors are reactors in which synthesis zone and/or condensation zone and/or scrubber zone are combined in a single vessel. Well-known examples are combination reactors as described in U.S. Pat. No. 5,767,313, U.S. Pat. No. 5,936,122 and WO 00/43358.

NL-A-8900152 discloses a process for the preparation of urea in which it is possible to increase the capacity of a urea production facility operating according to the stripping process without modifications of the high-pressure section of the urea synthesis being required.

This is achieved in NL-A-8900152 by preparing urea according to a process in which a urea synthesis solution containing urea, ammonium carbamate and unconverted ammonia is formed in a synthesis zone from carbon dioxide and ammonia, with a part of the urea synthesis solution being transferred to a medium-pressure treatment zone. In this medium-pressure treatment zone this amount of urea synthesis solution is contacted with an amount of carbon dioxide at a pressure of 1.5–3.0 MPa (medium pressure). In NL-A-89900152 the gas mixture formed in this medium-pressure treatment zone is condensed at medium pressure in a medium-pressure condensation zone, the heat formed during this condensation being used for evaporation of the urea solution in the urea recovery section. In NL-A-8900152 the residual urea synthesis solution leaving the medium-pressure treatment zone is transferred to a low-pressure recovery section (0.2–0.6 MPa), where the ammonium carbamate still present is largely decomposed and the gas mixture formed is separated.

Surprisingly, it has now been found possible to raise the capacity of a urea production facility without any modifications of the high-pressure section of the urea production facility being required and also to increase the urea conversion in the synthesis zone. This is all the more remarkable since as a rue the additional production resulting from an increase in the throughput in a urea production facility is in part lost due to a small decrease in urea conversion.

This advantage is achieved by preparation of urea according to a process, in which a urea synthesis solution containing urea, ammonium carbamate and unconverted ammonia is formed from carbon dioxide and ammonia in a synthesis zone
a part of the urea synthesis solution is transferred from the synthesis zone to a medium-pressure treatment zone operated at a pressure of 1–4 MPa, preferably 1.5–3.0 MPa, and the process is characterized in that a gas stream from the medium-pressure treatment zone is absorbed into the low-pressure ammonium carbamate solution from the urea recovery section. Low pressure here means a pressure of 0.1–1 MPa, in particular 0.2–0.7 MPa. In particular, 10–60 wt. % of the urea synthesis solution is fed to the medium-pressure treatment zone, more in particular 15–45 wt. %. Preferably, the stream from the medium-pressure treatment zone that is formed upon absorption of the gas stream from the medium-pressure treatment zone into the low-pressure ammonium carbamate solution from the recovery section is transferred to the high-pressure scrubber.

It has been found that during condensation of the gas stream from the medium-pressure treatment zone into the ammonium carbamate solution from the urea recovery section in this medium-pressure condensation zone the ammonium carbamate solution from the urea recovery section, with a water content of 25–35 wt. %, can be concentrated to a ammonium carbamate solution with a water content that is up to 10 wt. % lower, for example 15–25 wt. %. Since this ammonium carbamate solution is transferred to the synthesis zone via the high-pressure scrubber zone and high-pressure condensation zone, this means that less water is recirculated to the synthesis zone, which results in an increase in the efficiency of the synthesis zone. In the medium-pressure condensation zone heat is formed as a result of the formation of ammonium carbamate in this zone. By means of direct or indirect heat exchange this heat can be utilized elsewhere in the process for heating of process streams or for reduction by evaporation of the urea solution in the urea recovery section. This heat can also be discharged by means of cooling water.

Use of the process according to the invention surprisingly made it possible to expand the capacity of an existing urea production facility to about 120 to 150% of the original capacity without the need to expand or modify the high-pressure equipment, while the conversion in the urea synthesis increased by 0.5–3%, depending on the other process conditions. Such an increase in the capacity does require the installation of an extra treatment zone with associated piping, but the equipment needed for this is relatively cheap compared with the cost of high-pressure equipment. This extra treatment zone substantially comprises a medium-pressure dissociation zone, a medium-pressure stripping zone and a medium-pressure condensation zone. It is possible for two or three of these zones to be accommodated in a single vessel. Use of the process according to the invention ensures that the above-mentioned bottlenecks, viz. 'flooding' in the stripping zone and the risk of a too low pressure of the steam produced in the condensation zone, are avoided.

The process according to the invention can be performed in a urea production facility operating according to the stripping process. This is understood to mean a urea production facility in which the decomposition of the ammonium carbamate that has not been converted into urea and the expulsion of the customary excess ammonia for the most part takes place at a pressure that is essentially virtually the same as the pressure in the synthesis, zone. This decomposition/expulsion takes place in a stripping zone, optionally with addition of a stripping gas. In a stripping process carbon dioxide and/or ammonia can be used as stripping gas before these components are fed to the synthesis zone. This stripping takes place in a stripper installed downstream of the synthesis reactor, the urea synthesis solution leaving the synthesis reactor being stripped in countercurrent with the stripping gas while heat is being added. Use may also be made of thermal stripping. Thermal stripping means that use is made exclusively of the supply of heat to decompose ammonium carbamate and remove the ammonia and carbon dioxide contained in the urea solution. Stripping can also be performed in two or more steps. A process is known, for example, in which first exclusively thermal stripping takes place, after which a $CO_2$ stripping step is carried out with further supply of heat. The gas stream containing ammonia and carbon dioxide that leaves the stripper is returned to the synthesis zone. Stripping of the urea synthesis solution with a stripping medium can take place in more than one stripper. In processes using more than one stripper, the urea synthesis solution used as the feed to the medium-pressure treatment zone can be withdrawn from the outlet of the synthesis zone or from the liquid solution between these strippers.

In a urea production facility operating according to the stripping process the synthesis reactor is operated at a temperature of 160–240° C. and preferably at a temperature of 170–220° C. The pressure in the synthesis reactor is 12–21 MPa and preferably 12.5–19.5 MPa. The N/C ratio in the synthesis zone of a urea stripping plant is between 2.5 and 4. If the conversion into urea is carried out in two or more separate synthesis zones, with fresh raw materials preferably being supplied to one synthesis zone and recirculated raw materials preferably being supplied to a second synthesis zone, then the present invention is eminently suited to improve the efficiency in this second synthesis zone.

A frequently used embodiment for the preparation of urea according to a stripping process is the Stamicarbon $CO_2$ stripping process as for example described in Uhlmann's Encyclopedia of Industrial Chemistry, Vol. A27, pp. 344–346, 1996. The larger part of the gas mixture obtained in the stripping treatment is condensed and adsorbed together with the ammonia needed for the process in a condensation zone, for example in a high-pressure carbamate condenser, following which the resulting ammonium carbamate is transferred to the synthesis zone for the formation of urea.

The high-pressure carbamate condenser can for example be designed as a so-called submerged condenser as described in NL-A-8400839. The submerged condenser can be placed horizontally or vertically. Condensation in a horizontal submerged condenser (a so-called pool condenser; see for example Nitrogen No. 222, July–August 1996, pp. 29–31), however, offers special advantages, since in comparison with other designs of this condenser the liquid as a rule has a longer residence time in the pool condenser. As a result, extra urea formation takes place, which raises the boiling point, so that the temperature difference between the urea containing ammonium carbamate solution and the cooling medium increases and a better heat transfer is achieved.

The functions of reactor, high-pressure carbamate condenser and high-pressure scrubber can be combined in one or two high-pressure vessels, the functionalities of these process steps being separated by baffles designed for small pressure differences in these high-pressure vessels. This has as a special advantage that substantial savings can be realized in terms of investments as the amount of high-pressure piping to be installed is much lower. In addition, this increases the reliability of the facility since the number of leakage-sensitive high-pressure connections formed between piping and equipment is greatly reduced. Well-known examples are the combination reactors already referred to, as described in U.S. Pat. No. 5,767,313, U.S. Pat. No. 5,936,122 and WO 00/43358. A preferred embodiment is the combination of the pool condenser with a horizontal reactor as described in U.S. Pat. No. 5,767,313, in which a so-called pool reactor is represented.

After the stripping operation the stripped urea synthesis solution is expanded to a low pressure and reduced by evaporation in the urea recovery section, following which urea is liberated and a low-pressure ammonium carbamate stream is recirculated to the synthesis section. Depending on the type of stripping process the recovery of this ammonium carbamate can be carried out in a single process step or in several process steps operated at different pressures. In all variants the advantages with the process according to the invention are achieved.

In a special embodiment urea is prepared according to a process in which the reactor and high-pressure carbamate condenser are accommodated in a single vessel in the high-pressure section and in which a part of the urea synthesis solution is discharged to a medium-pressure treatment zone operating at a pressure of 1–4 MPa, preferably 1.5–3.0 MPa. In this embodiment the synthesis zone and high-pressure carbamate condenser may be accommodated in a horizontal or vertical vessel. Preferably the synthesis zone and high-pressure carbamate condenser are accommodated in a horizontally placed vessel, a so-called pool reactor. The advantage of the process according to the invention is that an investment advantage is achieved in the high-pressure section.

In this special embodiment urea is prepared according to a process in which a urea synthesis solution containing urea, ammonium carbamate and unconverted ammonia is formed from carbon dioxide and ammonia in a synthesis zone of a combination reactor with a part of the urea synthesis solution being transferred from the urea synthesis zone to a treatment zone operated at a pressure of 1–4 MPa, preferably 1.5–3.0 MPa, and with a gas stream from the medium-pressure treatment zone being absorbed into the low-pressure ammonium carbamate solution from the urea recovery section. Low pressure here means a pressure of 0.1–1 MPa, in particular 0.2–0.7 MPa. In particular 10–60 wt. % of the urea synthesis solution is fed to the medium-pressure treatment zone, more in particular 15–45 wt. %. As combination reactor use is preferably made of a vertically placed combination reactor or a pool reactor. More preferably use is made of a pool reactor. The stream from the medium-pressure treatment zone that is formed upon absorption of the gas stream from the medium-pressure treatment zone into the low-pressure ammonium carbamate solution from the recovery section is preferably transferred to the high-pressure scrubber.

The process according to the present process is carried out in a urea production facility operating according to the stripping process in which a urea synthesis solution containing urea, ammonium carbamate and unconverted ammonia is formed from carbon dioxide and ammonia in a synthesis zone a part of the ammonium carbamate in the urea synthesis solution decomposes in a high-pressure stripping zone as a result of a stripping treatment with a stripping gas with heating and at least a part of the resulting gas mixture is condensed in a condensation zone and the condensate and any non-condensed part are returned to the synthesis zone the ammonium carbamate still present in the residual urea synthesis solution at least largely decomposes in a low-pressure recovery section at a pressure of 0.1–1 MPa, preferably 0.2–0.7 MPa and the resulting gas mixture is separated, following which the residual urea-containing solution is processed further by evaporation to obtain a concentrated urea solution and optionally solid urea the gas mixture formed is condensed in the low-pressure recovery section, yielding a low-pressure ammonium carbamate stream that is returned to the process a part of the urea synthesis solution is passed from the synthesis zone to a treatment zone operating at a pressure of 1–4 MPa, preferably 1.5–3.0 MPa, an amount of carbon dioxide and optionally ammonia corresponding to the amount needed for the preparation of the supplied part of the urea synthesis solution is fed to this treatment zone and the solution discharged from the treatment zone is processed further in the low-pressure recovery section and the gas stream from the medium-pressure treatment zone being absorbed into the low-pressure ammonium carbamate solution from the urea recovery section.

Major advantages are achieved in particular when new urea preparation facilities are to be built ('grassroot plants') and in particular high-capacity plants. High-capacity plants are understood to be plants having a capacity of $1.5 \cdot 10^6$ kg to $6 \cdot 10^6$ kg product per day. When using the process according to the invention in particular the high-pressure carbamate condenser and the high-pressure stripper in the synthesis section of the urea production facility can be designed much smaller in comparison with the customary design. The high-pressure piping in this section also becomes much smaller when using this process, which also reduces investment. For 'grassroot plants' this may reduce the investment by 5–10%. In addition, the present invention implies that in 'grassroot' projects the high-pressure equipment used is still of a size that can readily be made by equipment manufacturers and that allows this equipment to be readily transported over large distances.

A further advantage that was found is that the process is particularly suited for the reduction of the consumption of energy in the form of high-pressure steam. For 'grassroot' projects the amount of high-pressure steam saved is approximately 30 to 100 kg per 1000 kg of product produced relative to the standard Stamicarbon $CO_2$ stripping process.

Since the turndown ratio of a stripping plant is determined by the size of the high-pressure stripper, the flexibility and hence the turndown ratio of a plant according to the above process is much higher than the turndown ratios of standard urea stripping plants. The turndown ratio of a plant is the minimum load on which a plant can be operated without turn-down time. Operation at minimum load may be necessary if the supply of raw materials is disrupted or strongly reduced. The advantage of the present invention then is that the medium-pressure treatment zone is a parallel section that can be switched off. A urea production facility having a capacity of $3.10^6$ kg per day and a turndown ratio of 60% can for example be operated at a minimum capacity of $1.8.10^6$ kg per day. If $1.10^6$ kg per day is discharged via the medium-pressure treatment zone the minimum capacity at which a urea production facility having the same capacity and the same turndown ratio can still be operated is $1.2.10^6$ kg per day.

With the process according to the present invention a capacity increase can be achieved in all existing urea processes operating according to the stripping process by feeding a part of the urea synthesis solution to an extra medium-pressure treatment zone comprising a medium-pressure dissociation zone, a medium-pressure stripping zone and a medium-pressure condensation zone.

Examples of urea stripping processes in which the process can be used include the Stamicarbon $CO_2$ stripping process, the Ammonia stripping process, the Self-stripping process, the ACES process (Advanced process for Cost and Energy Saving) and the IDR (Isobaric Double Recycle) process. These processes are described in Ullmann's Encyclopedia of Industrial Chemistry, Vol. A 27, 1996, pp. 344–350.

The invention will be elucidated with reference to FIGS. 1 up to and including 4.

Figure 1:
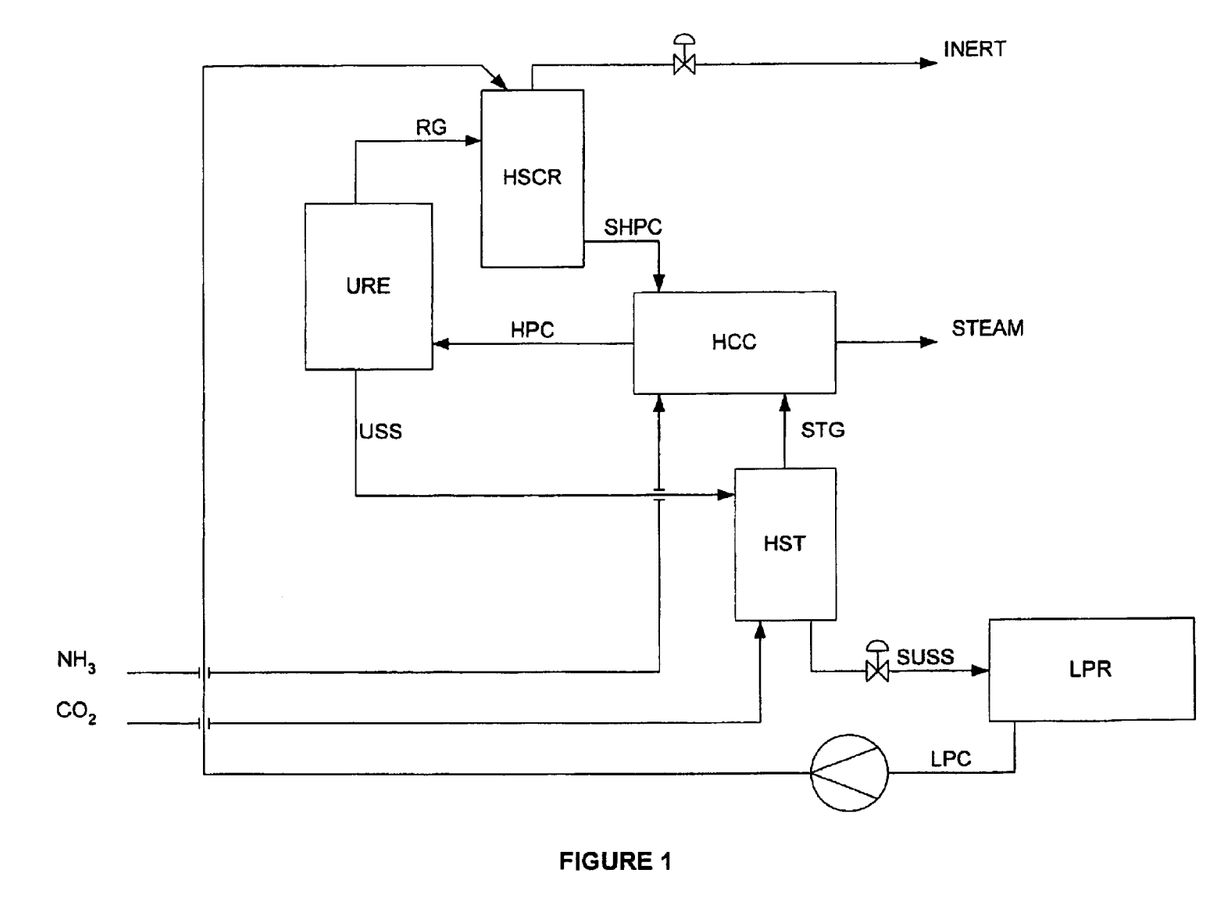
FIG. 1 schematically represents an urea process according to the Stamicarbon $CO_2$ stripping process.

FIG. 1

The urea solution (USS) leaving the urea reactor (URE) is sent to the high-pressure stripper (HST). In this high-pressure stripper unconverted ammonium carbamate is dissociated with the aid of high-pressure steam and carbon dioxide to form gaseous stripper gas (STG) substantially consisting of ammonia and carbon dioxide. The urea solution leaving the high-pressure stripper (SUSS) is fed to a low-pressure recovery section (LPR), where further purification of the urea solution takes place. The ammonia and carbon dioxide obtained in this recovery section are condensed and returned as low-pressure ammonium carbamate stream (LPC) to the high-pressure scrubber (HSCR) in the synthesis section. The gaseous ammonia and carbon dioxide leaving the high-pressure stripper (HST) are condensed in a high-pressure carbamate condenser (HCC). During the condensation of ammonia and carbon dioxide to form ammonium carbamate heat is released that is used to produce low-pressure steam. The amount of low-pressure steam produced is sufficient to meet the low-pressure steam needs of the urea recovery section. The high-pressure carbamate condenser (HCC) may be any design of submerged condenser or any design of a falling film type. Both embodiments are known to the man skilled in the art. The ammonium carbamate solution (HPC) formed in the HCC together with still freely present ammonia and carbon dioxide are fed to the urea reactor (URE). The fresh $NH_3$, too, is fed via the high-pressure carbamate condenser. During the synthesis reaction a gas stream, the synthesis gas (RG), is obtained in the reactor, which stream is sent to the HSCR. The synthesis gas substantially consists of ammonia, carbon dioxide and inert gases fed to the synthesis as corrosion inhibitor. These inert gases (air) are usually introduced into the process via the carbon dioxide feed. In the high-pressure scrubber the synthesis gas (RG) is absorbed into the low-pressure ammonium carbamate stream (LPC) from the urea recovery section. This results in a carbamate stream (SHPC), which is transferred to the high-pressure carbamate condenser. From the high-pressure scrubber the inerts are vented to the atmosphere, optionally after additional removal of any ammonia still present.

Figure 2:
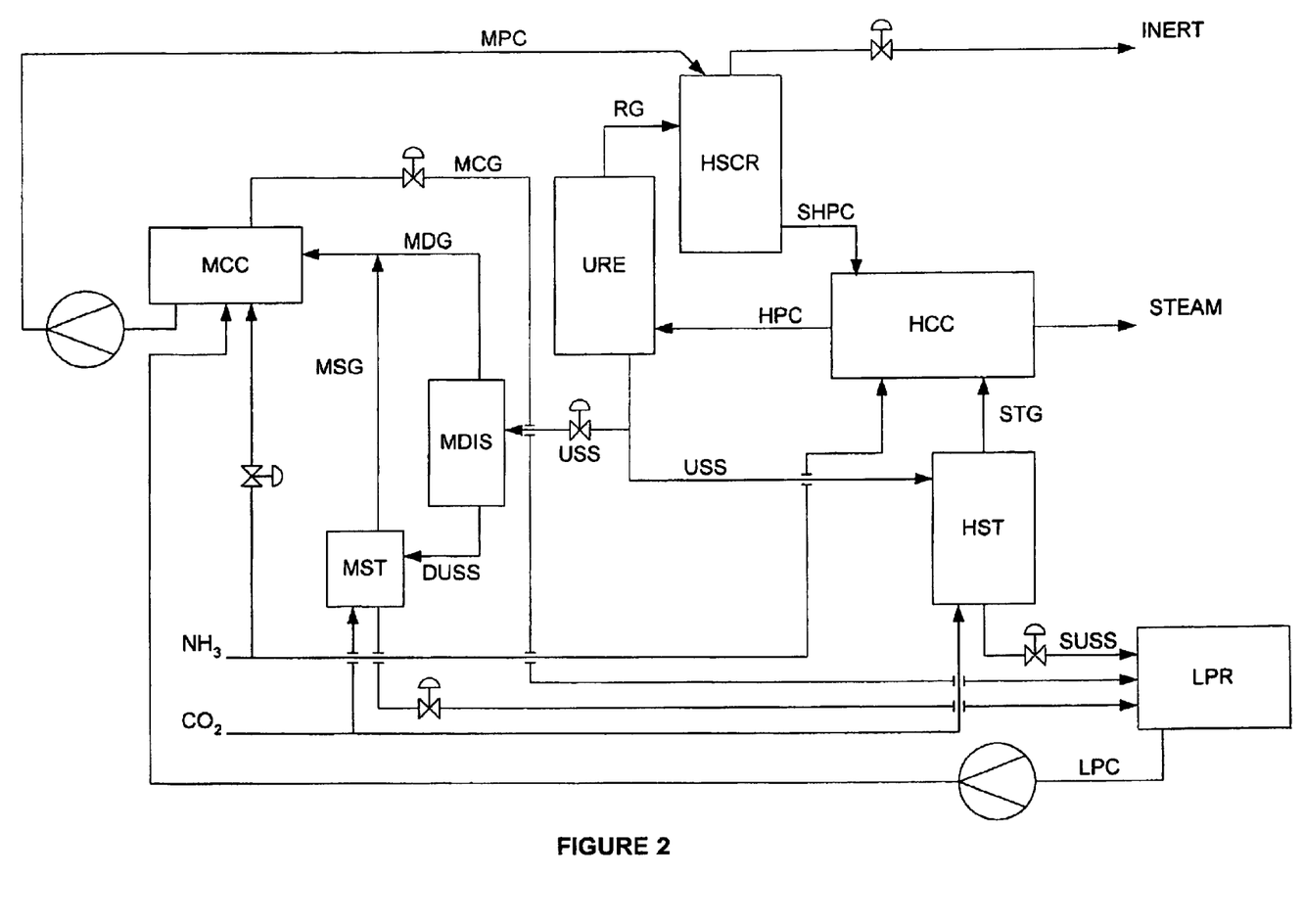
FIG. 2 schematically represents a urea process according to the Stamicarbon $CO_2$ stripping process in which a part of the urea synthesis solution is treated in a medium-pressure treatment zone via a bypass.

FIG. 2

A part of the urea solution (USS) leaving the urea reactor (URE) is sent to the high-pressure stripper (HST). In this high-pressure stripper unconverted ammonium carbamate is dissociated with the aid of high-pressure steam and a part of the carbon dioxide feed to form gaseous ammonia and carbon dioxide. The urea solution leaving the high-pressure stripper (SUSS) is fed to a low-pressure recovery section (LPR) where further purification of the urea solution takes place. The ammonia and carbon dioxide obtained in this low-pressure recovery section are condensed and returned, as a low-pressure ammonium carbamate stream (LPC), via a medium-pressure treatment zone (MCC) arranged in parallel with the high-pressure stripper, to the high-pressure scrubber (HSCR) in the synthesis zone. The heat produced upon condensation can be used for concentrating the urea solution in the recovery section. The gaseous ammonia and carbon dioxide leaving the high-pressure stripper (HST), the stripper gas (STG), is condensed in a high-pressure carbamate condenser (HCC). During the condensation of ammonia and carbon dioxide to form ammonium carbamate heat is released that is used to produce low-pressure steam. The amount of low-pressure steam produced is sufficient to meet the low-pressure steam needs in the urea recovery section. The high-pressure carbamate condenser (HCC) may be any design of submerged type or any design of falling film type. The ammonium carbamate solution formed, together with ammonia and carbon dioxide still freely present, are fed to the urea reactor (URE).

A part of the urea solution (USS) leaving the high-pressure reactor is sent to a medium-pressure treatment zone that is operated at a pressure of approximately 2 MPa. This medium-pressure treatment zone comprises a medium-pressure dissociation zone (MDIS), a medium-pressure stripping zone (MST) and a medium-pressure condensation zone (MCC). The unconverted ammonium carbamate in the USS is decomposed into gaseous ammonia and carbon dioxide in a medium-pressure dissociation zone (MDIS) by heat supply. The urea solution leaving this medium-pressure dissociation zone (DUSS), which contains relatively much ammonia, can be stripped with fresh carbon dioxide in a medium-pressure carbon dioxide stripper (MST). The urea solution leaving the MST is discharged to the low-pressure recirculation section (LPR). The off-gases (MDG) from the medium-pressure dissociation zone (MDIS), together with the off-gases (MSG) from the medium-pressure carbon dioxide stripper (MST), are condensed in a medium-pressure carbamate condenser (MCC) into the low-pressure ammonium carbamate stream (LPC) from the recovery section, yielding a concentrated medium-pressure ammonium carbamate stream (MPC), which is pumped to the high-pressure scrubber (HSCR). In this way the low-pressure ammonium carbamate (LPC) containing about 30% water is concentrated in the medium-pressure treatment zone to form ammonium carbamate (MPC) containing only 20% water. Using these data, the distribution between the amounts of urea solution fed to the high-pressure stripper (HST) and the medium-pressure dissociation zone (MDIS) is calculated, care being taken that the amount of water sent to the high-pressure scrubber via the medium-pressure ammonium carbamate is lower than or equal to the amount of water fed to such a high-pressure scrubber in a standard urea stripping plant. Due to the relatively smaller amount of urea solution to be treated in the high-pressure stripper, the dissociation of the urea solution at a lower pressure in the medium-pressure dissociation zone, which hence requires less energy, and a lower or equal water feed to the high-pressure scrubber via the ammonium carbamate stream (MPC), the high-pressure steam consumption in plants operating according to this process is lower than in standard urea $CO_2$ stripping plants. If desirable, the $NH_3$ needed for the process is proportionally fed via the MCC and HCC. The gas mixture not condensed in the medium-pressure carbamate condenser is transferred as a gas stream (MCG) to the low-pressure recovery section, where it is processed further. The synthesis gas (RG) is absorbed into the medium-pressure ammonium carbamate stream in the high-pressure scrubber, so that a further ammonium carbamate stream is formed. From the high-pressure scrubber this ammonium carbamate stream (SHPC) is transferred to the high-pressure carbamate condenser. The inert gases are vented from the high-pressure scrubber, optionally after an extra purification step to remove any $NH_3$ still present.

Figure 3:
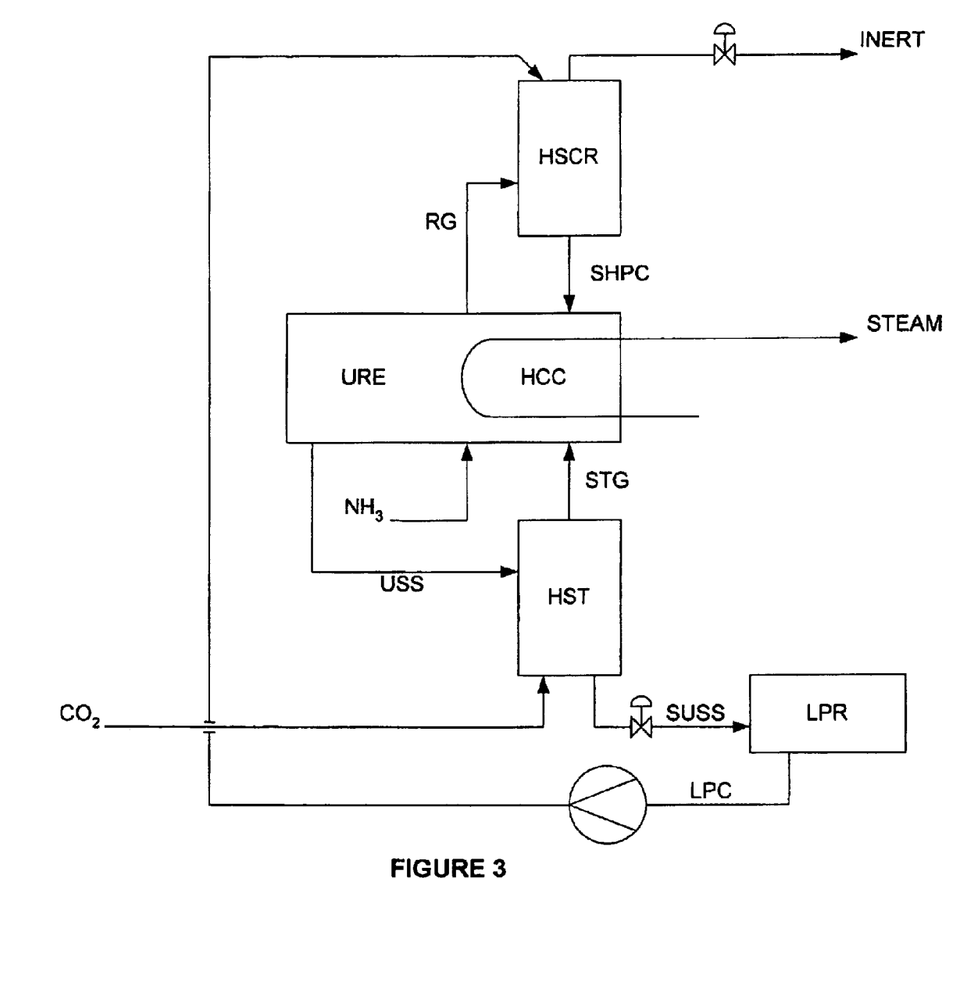
FIG. 3 schematically represents a Stamicarbon $CO_2$ stripping process with a pool reactor according to U.S. Pat. No. 5,767,313.

FIG. 3

The urea solution (USS) leaving the urea pool reactor (URE+HCC) is sent to the high-pressure stripper (HST). In this high-pressure stripper unconverted ammonium carbamate is dissociated into gaseous ammonia and carbon dioxide using high-pressure steam and carbon dioxide feed. The urea solution (SUSS) leaving the high-pressure stripper is fed to a low-pressure recovery section (LPR), where further purification of the urea solution takes place. The ammonia and carbon dioxide obtained in this low-pressure recirculation section are condensed and returned as a low-pressure ammonium carbamate stream (LPC) to the high-pressure scrubber (HSCR) in the synthesis section. In this scrubber ammonia and carbon dioxide are absorbed from the synthesis gas (RG), following which an inerts stream is vented and a high-pressure carbamate stream (SHPC) formed in the scrubber is transferred to the pool reactor. The gaseous stream (STG), mainly containing ammonia and carbon dioxide, which leaves the high-pressure stripper (HST) is condensed in a high-pressure carbamate condenser (HCC) section of the pool reactor. During the condensation of ammonia and carbon dioxide to form ammonium carbamate heat is released that is used to produce low-pressure steam. The amount of low-pressure steam produced is sufficient to meet the needs in this respect in the urea recovery section. The high-pressure carbamate condenser (HCC) is of a so-called submerged type and is located in the pool reactor. The $NH_3$ needed for the process is fed directly to the pool reactor.

Figure 4:
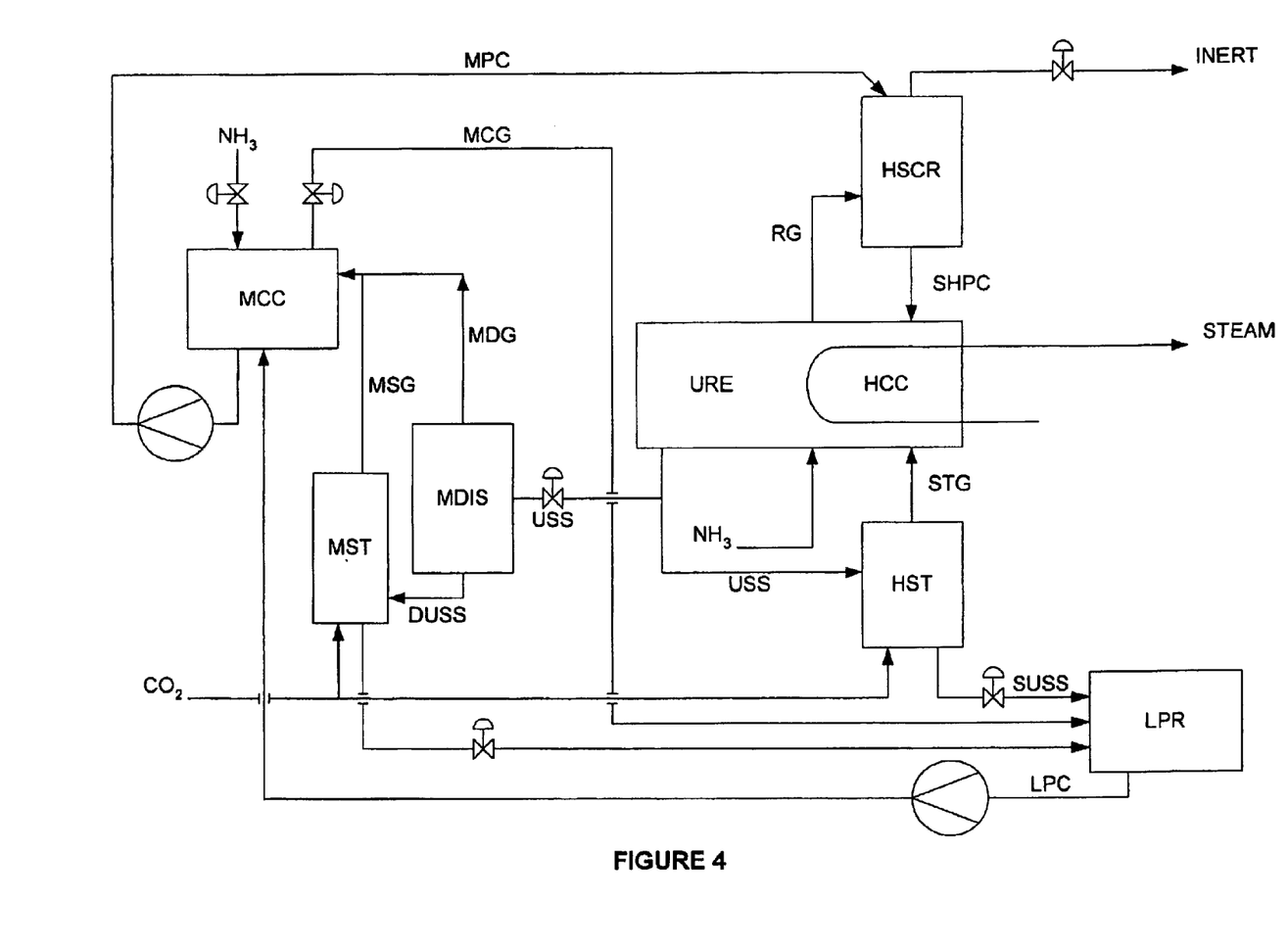
FIG. 4 schematically represents a Stamicarbon $CO_2$ stripping process with a pool reactor according to U.S. Pat. No. 5,767,313 in which a part of the urea synthesis solution is treated in a medium-pressure treatment zone via a bypass.

FIG. 4

Part of the urea solution (USS) leaving the urea pool reactor (URE+HCC) is sent to the high-pressure stripper (HST). In this high-pressure stripper unconverted ammonium carbamate is dissociated into gaseous ammonia and carbon dioxide with the aid of high-pressure steam and a part of the carbon dioxide feed. The urea solution (SUSS) leaving the high-pressure stripper is sent to a low-pressure recovery section (LPR), where further purification of the urea solution takes place. The ammonia and carbon dioxide obtained in this low-pressure recovery section are condensed and returned as low-pressure ammonium carbamate stream (LPC), via a medium-pressure treatment zone arranged in parallel with the high-pressure stripper, to the high-pressure scrubber (HSCR) in the synthesis section. The medium-pressure treatment zone comprises a medium-pressure dissociation zone (MDIS), a medium-pressure stripping zone (MST) and a medium-pressure condensation zone (MCC). The stream containing gaseous ammonia and carbon dioxide (STG) leaving the high-pressure stripper (HST) is condensed in a high-pressure carbamate condenser (HCC) section of the pool reactor. During the condensation of ammonia and carbon dioxide to form ammonium carbamate heat is released that is used to produce low-pressure steam. The amount of low-pressure steam produced is sufficient to meet the needs in this respect in the urea recovery section. The high-pressure carbamate condenser (HCC) is of a so-called submerged type and is located in the pool reactor. A part of the urea solution (USS) leaving the high-pressure pool reactor is sent to a medium-pressure treatment zone that is operated at a pressure of about 2 MPa. The unconverted ammonium carbamate is decomposed into gaseous ammonia and carbon dioxide by heat supply in a medium-pressure dissociation zone (MDIS). The urea solution leaving this medium-pressure dissociation zone (DUSS), which contains relatively much ammonia, can be stripped in a medium-pressure carbon dioxide stripper (MST) with a part of the fresh carbon dioxide. The urea solution leaving the medium-pressure carbon dioxide stripper is discharged to the low-pressure recovery section (LPR). The off-gases from the medium-pressure dissociation zone (MDG), together with the off-gases from the medium-pressure carbon dioxide stripper (MSG), are sent to a medium-pressure carbamate condenser (MCC) for condensation in the low-pressure ammonium carbamate stream (LPC) obtained in the recovery section. The heat of condensation released in this MCC is utilized by direct heat exchange with the urea solution in the recovery section, as a result of which the urea solution is concentrated. The ammonium carbamate leaving the medium-pressure carbamate condenser is pumped to the high-pressure scrubber (HSCR). In this way the low-pressure ammonium carbamate, which contains about 30% water, is concentrated in the medium-pressure treatment zone to ammonium carbamate containing only 20% water. Using these data, also the distribution between the amount of urea solution going to the high-pressure stripper (HST) and that going to the medium-pressure dissociation zone (MDIS) is calculated, care being taken that the amount of water sent to the high-pressure scrubber via the medium-pressure ammonium carbamate is lower than or equal to the amount of water sent to such a high-pressure scrubber in a standard urea stripping plant. Due to the increased synthesis efficiency, there is relatively less urea solution to be treated in the high-pressure stripper. As a consequence this stripper will use less steam. The gas mixture that is not condensed in the medium-pressure carbamate condenser (MCC) is transferred as a gas stream (MCG) to the low-pressure recovery section (LPR). In the high-pressure scrubber (HSCR) the synthesis gas (RG) is absorbed into the medium-pressure ammonium carbamate stream (MPC), yielding a concentrated ammonium carbamate stream (SHPC) that is transferred to the pool reactor. From the HSCR the inert gases are removed from the system.

What is claimed is:

1. Process for the preparation of urea from ammonia and carbon dioxide in which a urea synthesis solution containing urea, ammonium carbamate and unconverted ammonia is formed in a synthesis zone, a part of the urea synthesis solution being transferred from the synthesis zone to a medium-pressure treatment zone operating at a pressure of 1–4 MPa, wherein a gas stream from the medium-pressure treatment zone is absorbed into the low-pressure ammonium carbamate solution from the urea recovery section.

2. Process according to claim 1, wherein the pressure in the medium-pressure treatment zone is 1.5–3.0 MPa.

3. Process according to claim 1, wherein 10–60 wt. % of the urea synthesis solution is fed to the medium-pressure treatment zone.

4. Process according to claim 1, wherein the stream from the medium-pressure treatment zone that is formed upon absorption of the gas stream from the medium-pressure treatment zone into the low-pressure ammonium carbamate solution from the recovery section is transferred to the high-pressure scrubber.

5. Process for the preparation of urea from ammonia and carbon dioxide in which a urea synthesis solution containing urea, ammonium carbamate and unconverted ammonia is formed in a synthesis zone of a combination reactor, wherein a part of the urea synthesis solution is transferred from the urea synthesis zone to a treatment zone operating at a pressure of 1–4 MPa and in which a gas stream from the medium-pressure treatment zone is absorbed into the low-pressure ammonium carbamate solution from the urea recovery section.

6. Process according to claim 5, wherein the pressure in the medium-pressure treatment zone is 1.5–3.0 MPa.

7. Process according to claim 5, wherein 10–60 wt. % of the urea synthesis solution is fed to the medium-pressure treatment zone.

8. Process according to claim 5, wherein as combination reactor use is made of a vertically placed combination reactor or a pool reactor.

9. Process according to claim 8, wherein as combination reactor use is made of a pool reactor.

10. Method for increasing the capacity of existing urea processes by feeding a part of the urea synthesis solution to an additionally installed medium-pressure treatment zone comprising a dissociation zone, a medium-pressure stripping zone and a medium-pressure condensation zone.

* * * * *